US006979440B2

(12) United States Patent
Shefer et al.

(10) Patent No.: US 6,979,440 B2
(45) Date of Patent: Dec. 27, 2005

(54) COMPOSITIONS AND METHOD FOR TARGETED CONTROLLED DELIVERY OF ACTIVE INGREDIENTS AND SENSORY MARKERS ONTO HAIR, SKIN, AND FABRIC

(75) Inventors: Adi Shefer, East Brunswick, NJ (US); Samuel David Shefer, East Brunswick, NJ (US)

(73) Assignee: Salvona, LLC, Dayton, NJ (US)

( * ) Notice: Subject to any disclaimer, the term of this patent is extended or adjusted under 35 U.S.C. 154(b) by 319 days.

(21) Appl. No.: 10/222,054

(22) Filed: Aug. 16, 2002

(65) Prior Publication Data
US 2003/0053974 A1 Mar. 20, 2003

Related U.S. Application Data

(63) Continuation-in-part of application No. 09/771,752, filed on Jan. 29, 2001, now Pat. No. 6,491,902.

(51) Int. Cl.[7] ............................................ A61K 31/74
(52) U.S. Cl. ................. 424/78.02; 424/78.03
(58) Field of Search ................ 424/401, 70.1, 424/78.01; 252/8.8; 510/515

(56) References Cited

U.S. PATENT DOCUMENTS

| | | | |
|---|---|---|---|
| 3,980,091 A | 9/1976 | Dasher et al. .................. 132/7 |
| 4,152,272 A * | 5/1979 | Young ......................... 252/8.8 |
| 4,942,038 A | 7/1990 | Wallach ....................... 424/450 |
| 5,037,818 A | 8/1991 | Sime .......................... 514/183 |
| 5,085,857 A | 2/1992 | Reid et al. ..................... 424/70 |
| 5,124,081 A | 6/1992 | Vanlerberghe et al. ....... 424/450 |
| 5,198,470 A | 3/1993 | Zysman et al. ............. 514/785 |
| 5,330,758 A | 7/1994 | Hansenne-Richoux et al. ........................... 424/450 |
| 5,354,564 A | 10/1994 | Borish et al. ............... 424/490 |
| 5,476,660 A | 12/1995 | Somasundaran et al. .... 424/401 |
| 5,510,120 A | 4/1996 | Jones et al. .................. 424/499 |
| 5,518,736 A | 5/1996 | Magdassi et al. ........... 424/451 |
| 5,556,616 A | 9/1996 | Janchitraponvej et al. ....................... 424/70.122 |
| 5,591,449 A | 1/1997 | Bollens et al. .............. 424/450 |
| 5,599,531 A | 2/1997 | Holcomb ................... 424/70.1 |
| 5,658,575 A | 8/1997 | Ribier et al. ................ 424/401 |
| 5,660,839 A | 8/1997 | Allec et al. ................. 424/401 |
| 5,660,853 A | 8/1997 | Hansenne-Richoux ...... 424/450 |
| 5,667,800 A | 9/1997 | De Vringer ................. 424/450 |
| 5,741,518 A | 4/1998 | Ribier et al. ................ 424/450 |
| 5,753,241 A | 5/1998 | Ribier et al. ................ 424/401 |
| 5,759,526 A | 6/1998 | Simonnet et al. ............. 424/59 |
| 5,773,611 A | 6/1998 | Zysman et al. ............. 424/401 |
| 5,780,060 A | 7/1998 | Levy et al. ................. 424/489 |
| 5,814,343 A | 9/1998 | Jones et al. .................. 424/499 |
| 5,843,875 A | 12/1998 | Wei et al. .................... 510/101 |
| 5,851,517 A | 12/1998 | Mougin et al. .......... 424/78.02 |
| 5,874,105 A | 2/1999 | Watkins et al. ............. 424/450 |
| 5,885,564 A | 3/1999 | Zastrow et al. ............... 424/74 |
| 5,919,487 A | 7/1999 | Simonnet et al. ........... 424/490 |
| 5,925,364 A | 7/1999 | Ribier et al. ................ 424/401 |
| 5,945,095 A | 8/1999 | Mougin et al. .......... 424/78.02 |
| 5,962,018 A | 10/1999 | Curtis et al. ................ 424/450 |
| 6,010,707 A | 1/2000 | Philippe et al. ............. 424/401 |
| 6,013,618 A | 1/2000 | Morelli et al. ................. 512/1 |
| 6,015,574 A | 1/2000 | Cannell et al. ............. 424/450 |
| 6,039,936 A | 3/2000 | Restle et al. ............... 424/70.1 |
| 6,042,792 A * | 3/2000 | Shefer et al. ............... 422/259 |
| 6,048,520 A | 4/2000 | Hoshowski ............... 424/70.17 |
| 6,066,328 A | 5/2000 | Ribier et al. ................ 424/401 |
| 6,071,535 A | 6/2000 | Hayward et al. ........... 424/450 |
| 6,083,899 A * | 7/2000 | Baker et al. ................ 510/515 |
| 6,087,322 A | 7/2000 | Morelli et al. ................ 512/25 |
| 6,126,948 A | 10/2000 | Simonnet et al. ........... 424/401 |
| 6,491,902 B2 * | 12/2002 | Shefer et al. .............. 424/70.1 |

FOREIGN PATENT DOCUMENTS

| | | |
|---|---|---|
| EP | 0 386 898 | 2/1990 |
| WO | WO 95/22311 | 8/1995 |
| WO | WO 02/38713 | 5/2002 |
| WO | WO 02/060399 | 8/2002 |

\* cited by examiner

Primary Examiner—Thurman K. Page
Assistant Examiner—Sharon Howard
(74) Attorney, Agent, or Firm—Mathews, Shepherd, McKay & Bruneau, P.A.

(57) ABSTRACT

The present invention is a controlled delivery system that can be incorporated in hair, skin, and fabric care products such as shampoos, conditioners, hair styling products, lotions, creams, liquid laundry detergents, fabric softener, and other hair, skin, and fabric care products to effectively deliver a broad range of active agents and sensory markers onto the hair, skin, and fabric. The system also prolongs the release rate of the active agents or sensory markers over an extended period of time, or provides heat triggered release of the active agents and yields a high impact fragrance "burst" upon blow drying the hair, ironing the fabric, or other types of heat treatment. The controlled delivery system of the present invention is a nano-sphere, having an average sphere diameter of from about 0.01 microns to about 10 microns. The nano-sphere comprises hydrophobic materials, cationic conditioning agent or, cationic conditioning agent in conjunction with a cationic charge booster to assist in adhering the spheres onto hair, skin, and fabric. The invention further relates to a controlled delivery system where the release rate of the active ingredients is synchronized with that of a sensory marker to convey to the consumer the product performance.

63 Claims, 1 Drawing Sheet

COMPOSITIONS AND METHOD FOR TARGETED CONTROLLED DELIVERY OF ACTIVE INGREDIENTS AND SENSORY MARKERS ONTO HAIR, SKIN, AND FABRIC

This application is a continuation in part of U.S. Ser. No. 09/771,752, filed Jan. 29, 2001 Now U.S. Pat. No. 6,491,902, the contents of which are hereby incorporated by reference into this application.

BACKGROUND OF THE INVENTION

1. Field of the Invention

The present invention relates to a targeted controlled release system that can be incorporated into hair, skin, and fabric care products such as shampoos, conditioners, lotions, creams, body wash, liquid laundry detergent, fabric softener, and other hair, skin, and fabric care products that effectively delivers a broad range of active ingredients and sensory markers onto hair, hair follicles, skin, and fabric, prolongs their release rate over an extended period of time, or provides heat triggered release of active ingredients and high impact fragrance "burst" upon blow drying the hair or ironing the fabric. The invention further relates to skin, hair, and fabric care products comprising the targeted controlled release system of the present invention.

2. Description of the Related Art

Consumers are becoming increasingly educated and expect a high level of sophistication and multi functionality in their products. They expect that these products, not only to clean, but also condition, nourish, and provide a lasting impression of clean and freshness. Consumer acceptance of products is determined not only by the performance achieved with these products but the perception and aesthetics associated therewith. There is also a need to convey to the consumer the product performance and effectiveness (i.e., the hair, skin, or fabric is clean, the hair and skin are being conditioned and nourished, etc.). Fragrance is an important aspect of the successful products and they can also be utilized, in addition to imparting an aesthetically pleasing odor, to convey the consumer the product performance.

Publications in the prior art indicate attempts to fulfill the foregoing needs to increase the deposition of active ingredients and sensory markers (fragrances, cooling and heating agents, etc.) onto hair, skin, and fabric to hinder or delay their release rate so that the hair and skin are healthier and remains aesthetically pleasing for a prolonged length of time.

A conventional approach that has been described employs emulsions, liposomes, and other lipid vesicles to deposit the active ingredients onto the hair and skin. See U.S. Pat. Nos. 4,942,038; 5,124,081; 5,198,470; 5,330,758; 5,510,120; 5,518,736; 5,591,449; 5,658,575; 5,660,853; 5,741,518; 5,753,241; 5,759,526; 5,773,611; 5,814,343; 5,874,105; 5,885,564; 5,925,364; 6,010,707; 6,015,574; 6,039,936; 6,066,328; 6,071,535; and 6,126,948. These types of systems have the limitation of being unstable, and can only be used for encapsulation of certain types of materials. Stability has limited the use of liposomes for controlled delivery, both in terms of shelf life and after administration.

U.S. Pat. No. 5,354,564 discloses personal care products comprising an aqueous dispersion of particles of silicone wherein said particles have a surface modifier adsorbed on the surface thereof in an amount sufficient to achieve a particle size of less than about 400 nanometers (nm). The particles of this invention contain a discrete phase of silicone having a surface modifier adsorbed on the surface thereof. Suitable surface modifiers can preferably be selected from known organic and inorganic excipients. Such excipients include various polymers, low molecular weight oligomers, natural products and surfactants. Preferred surface modifiers include nonionic and anionic surfactants.

U.S. Pat. No. 5,599,531 discloses the uses of inorganic charged colloidal silica as a carrier system for hair care products. The penetration or absorption of water, oils, collagen, and other materials into the hair is greatly increased by adding a small quantity of inorganic charged colloidal silica to provide an aqueous suspension of the charged colloidal silica particles along with the material to be absorbed into the hair. In coloring hair, dye components can be absorbed into the hair without the use of alkaline solutions which damage the hair, and in perming hair, the disulfide bonds in the hair can be broken by tension caused by swelling due to water absorption in the hair, again without the use of damaging alkaline solutions. It is believed that the porosity and stable hydration of the hair can be varied through altering the electrostatic charge on the hair. The aqueous suspension of charged silica particles applied to the hair appears to alter this charge.

U.S. Pat. No. 5,660,839 discloses incorporating deformable hollow particles into cosmetic and/or dermatological compositions containing fatty substances, for markedly reduce or eliminate the sticky and/or greasy feel attributed to these fatty substances. Preferably, the particles are in the form of hollow microspheres or microbeads, having a particle size ranging from 1 micron to 250 microns, and comprising a copolymer of vinylidene chloride, acrylonitrile and a (meth)acrylate co monomer.

U.S. Pat. No. 5,667,800 discloses an aqueous suspension of solid lipoid nanoparticles, comprising at least one lipid and preferably also at least one emulsifier, for topical application to the body. The nano-particles disclosed are preferably non-ionic and the emulsifiers used in the processing of these particles are preferably chosen from the groups of polyoxyethylene alkyl ethers and sorbitan esters. The particles have a mean particle size of between 50–1000 nm and their concentration is between 0.01–60 wt %, by weight of the suspension. A medicament can be incorporated into the continuous phase of the suspension or in a vehicle, which is added to the suspension. The invention further provides manufacturing methods for the aqueous suspension.

U.S. Pat. No. 5,780,060 discloses microcapsules with a wall of crosslinked plant polyphenols and compositions containing them. The microcapsules are obtained by the interfacial crosslinking of plant polyphenols, particularly flavonoids. When incorporated in a composition such as a cosmetic, pharmaceutical, dietetic or food composition, these microcapsules make it possible to prevent any impairment of this composition, in particular any color modification, while at the same time preserving the activity, especially the anti-free radical and/or antioxidizing activity, of the plant polyphenols, particularly the flavonoids.

U.S. Pat. Nos. 5,851,517 and 5,945,095 disclose compositions including a dispersion of polymer particles in a non-aqueous medium. A dispersion of surface-stabilized polymer particles can be used in a non-aqueous medium, in a cosmetic, hygiene or pharmaceutical composition. The dispersions may, in particular, be in the form of nano-particles of polymers in stable dispersion in a non-aqueous medium. The nano-particles are preferably between 5 and 600 nm in size, given that beyond about 600 nm, the particle dispersions become much less stable. The polymers used can be of any nature, such as radical polymers, polycondensates or polymers of natural origin. These polymers may, in particular, be crosslinked. Among the non-film-forming polymers described are vinyl or acrylic radical copolymers or homopolymers, which are optionally crosslinked, preferably having a Tg of greater than or equal to 40 degree C., such as polymethyl methacrylate, polystyrene, or poly-tert-butyl acrylate.

U.S. Pat. Nos. 5,759,526 and 5,919,487 disclose nanoparticles coated with a lamellar phase based on silicone surfactant and compositions containing them. The nanoparticles, and in particular nanocapsules, provided with a lamellar coating obtained from a silicone surfactant, can be used in a composition, in particular a topical composition, for treatment of the skin, mucosae, nails, scalp and/or hair. Nanoparticles ranging in size from 10 to 1000 nm are composed of a polymer encapsulating an oily phase and coated with a lamellar coating, wherein the lamellar coating comprises at least one silicone surfactant containing at least a oxyethylenated and/or oxypropylenated chain. The nanoparticles preferably range in size from 10 to 600 nm. The polymers constituting the nanoparticles can be biodegradable or non-biodegradable polymers. Poly-L- and -DL-lactides and polycaprolactones are especially preferred as biodegradable polymers. Among non-biodegradable polymers, copolymers of vinyl chloride and vinyl acetate and copolymers of methacrylic acid and methacrylic acid methyl ester are especially preferred.

U.S. Pat. Nos. 6,013,618 and 6,087,322 disclose the use of pro-accords as a method to enhance fragrance performance from personal care products. Typically the pro-accords are comprised of orthoesters, ketals, acetals, orthocarbonates which release two or more fragrance raw materials upon hydrolysis.

U.S. Pat. No. 6,042,792 discloses a controlled, time-release microparticulate active and bioactive compositions (including perfuming compositions) for targeted delivery to services such as skin, hair and fabric and the environment proximate thereto, where the active and bioactive materials have a calculated log P values of between 1 and 8 (P being the n-octanol-water partition coefficient). Such compositions include the active or bioactive material in single phase, solid solution in a wax or polymer matrix also having coated thereon and/or containing a compatible surfactant. Also described are processes and apparatus for preparing such compositions. The emphasis of U.S. Pat. No. 6,042,792 is in engineering the fragrance formulation and thus limiting the type of fragrances that can be used with the system. The creation of such composition also requires the use of surfactant or emulsifier, which can increase the partition of the fragrance into the aqueous phase and reduce encapsulation efficacy and the amount of fragrance being deposited on the target site.

U.S. Pat. No. 4,152,272 discloses fabric conditioning compositions containing particles of size 0.1 to 200 microns and of melting point 38 degrees C. to 150 degrees C. and comprising a wax-like carrier substance and a perfume. The particles are distributed throughout a composition, especially an aqueous fabric softening composition which contains a fabric-substantive cationic surfactant. Cetyl trimethyl ammonium bromide is described as an example of the cationic surfactant.

U.S. Pat. No. 5,188,837 discloses a microsuspension system and method for its preparation. The microsuspension contains liposheres which are solid, water-insoluble microparticles that have a layer of a phospholipid embedded on their surface. The core of the liposphere is a solid substance to be delivered or a substance to be delivered that is dispersed in an inert solid vehicle such as a wax.

U.S. Pat. No. 5,540,853 discloses a personal cleansing composition comprising:
(a) from about 0.001% up to about 10% by weight of an enduring perfume composition having at least about 70% components with a calculated log.sub.10 P.gtoreq.3 and a boiling point of 250 degree C.;
(b) from about 0.01% up to about 95% by weight of a surfactant system; and
(c) the balance comprising carrier wherein the pH is from about 4 up to about 11. The disclosure of Trinh, et al, U.S. Pat. No. 5,540,853 is incorporated by reference herein.

U.S. Pat. No. 5,476,660 discloses compositions to deposit an active substance on a target surface. The active substance is left on the surface after the product is rinsed off the surface. The preferred deposition is from compositions containing an anionic or nonionic active in the co-presence of an anionic surfactant. The compositions contain carrier particles having a zwitterionic or cationic surface and a plurality of outwardly protruding filaments containing charged organocarbyl groups. The active substance is contained within the carrier particles. Examples of target surfaces are mammalian skin, hair or nails.

U.S. Pat. No. 5,652,206 discloses a rinse-added fabric softening composition selected from the group consisting of:
I. a solid particulate composition comprising:
(A) from about 50% to about 95% of biodegradable cationic quaternary ammonium fabric softening compound:
(B) from about 0.01% to about 15% of an enduring perfume comprising at least 70% of enduring perfume ingredients selected from the group consisting of: ingredients having a boiling point of at least about 250 degrees C. and a ClogP of at least about 3, wherein ClogP is the calculated octanol/water partitioning coefficient as the logarithm to the base 10 logP, said ingredients having a boiling point of at least 250 degrees C. and a ClogP of at least about 3 being less than 70% by weight of said enduring perfume so that a perfume with only ingredients having a boiling point of at least about 250 degrees C. and a ClogP of at least about 3 will not be an enduring perfume; cis-jasmone; dimethyl benzyl carbinyl acetate; ethyl vanillin; geranyl acetate; .alpha.-ionone; .beta.-ionone; gamma.-ionone; KOAVONE®; lauric aldehyde; methyl dihydrojasmonate; methyl nonyl acetaldehyde; .gamma.-nonalactone; phenoxy ethyl iso-butyrate; phenyl ethyl dimethyl carbinol; phenyl ethyl dimethyl carbinyl acetate; .alpha.-methyl-4-(2-methylpropyl)-benzenepropanal; 6-acetyl-1, 1,3,4,4,6-hexamethyl tetrahydronaphthalene; undecylenic aldehyde; vanillin; 2,5,5-trimethyl-2-pentyl-cyclopentanone; 2-tert-butylcyclohexanol; verdox; para-tert-butyl-cyclohexyl acetate; and mixtures thereof;
(C) optionally, from about 0% to about 30% of dispersibility modifier; and
(D) optionally, from about 0% to about 15% of a pH modifier; and
II. a liquid composition comprising:
(A) from about 0.5% to about 80% of biodegradable cationic fabric softening compound;
(B) from about 0.01% to about 10% of an enduring perfume comprising at least 70% of enduring perfume ingredients selected from the group consisting of: ingredients having a boiling point of at least about 250 degrees C. and a ClogP of at least about 3, said ingredients having a boiling point of at least about 250 degrees C. and a ClogP of at least about 3 being less than 70% by weight of said enduring perfume so that a perfume with only ingredients having a boiling point of at least about 250 degrees C. and a ClogP of at least about 3 will not be an enduring perfume; cis-jasmone; dimethyl benzyl carbinyl acetate; ethyl vanillin; geranyl acetate; .alpha.-ionone; .beta.-ionone; .gamma.-ionone; KOAVONE®; lauric aldehyde; methyl dihydrojasmonate; methyl nonyl acetaldehyde; .gamma.-nonalactone; phenoxy ethyl iso-butyrate; phenyl ethyl dimethyl carbinol; phenyl ethyl dimethyl carbinyl acetate; .alpha.-methyl-4-(2-methylpropyl)-benzenepropanal; 6-acetyl-1,1,3,4,4,6-hexamethyl tetrahydronaphthalene; undecylenic aldehyde; vanillin; 2,5,5-trimethyl-2-pentyl-cyclopentanone; 2-tert-butylcyclohexanol; verdox; para-tert-butylcylohexyl acetate; and mixtures thereof;

(C) optionally, from about 0% to about 30% of dispersibility modifier; and (D) the balance comprising a liquid carrier selected from the group consisting of water, $C_{1-4}$ monohydric alcohol; $C_{2-6}$ polyhydric alcohol; propylene carbonate; liquid polyethylene glycols; and mixtures thereof; and wherein the dispersibility modifier affects the viscosity, dispersibility or both.

U.S. Pat. No. 4,919,841 discloses a process for preparing encapsulated active particles by the steps of: dispersing active materials in molten wax; emulsifying the active/wax dispersion in an aqueous surfactant solution for no longer than 4 minutes; quenching the capsules by cooling; and retrieving solidified capsules. Examples of active materials are fragrances.

PCT Published Application No. 95/11936 published on Oct. 20, 1994 discloses finely dispersed wax dispersions with a long shelf life which can be obtained by heating: (A) 10 to 80 weight percent of a wax with (B) 0.5 to 30 weight percent of a hydrophilic nonionic dispersant with an HLB value of 8 to 18 and (C) 1 to 30 weight percent of a hydrophobic co-dispersant from the group of fatty alcohols with 12–22 carbon atoms or the partial esters of polyols with 3–6 carbon atoms with fatty acids with 12–22 carbon atoms, and then heating the dispersion obtained to a temperature within or above the phase inversion point or producing a dispersion directly at this temperature and subsequently cooling the dispersion to a temperature below the phase inversion range.

U.S. Pat. No. 6,048,520 discloses a transparent leave-on hair treatment composition including capsules of a water insoluble hair-treating compound encased in a shell material, such as gelatin or acacia gum. The capsules have a diameter of about 425 to about 2800 microns and are broken during application of the hair treatment composition to hair or by combing the hair after application of the hair treatment composition. The aqueous leave-on composition is applied to the hair and the water insoluble hair-treating compound is released from the capsules to treat the hair. The shell disintegrates into sufficiently small residual particles such that the physical and esthetic properties of the hair, like shine and comb ability, are retained.

Cationic deposition polymers have been conventionally used to enhance deposition of certain nonvolatile components from shampoos and other personal cleansing compositions. For example, U.S. Pat. Nos. 5,037,818 and 5,085,857 describe the use of cationic guar gum to enhance the deposition of antidandruff particles and insoluble nonvolatile silicone, respectively. Deposition polymers have also been proposed to enhance the deposition of sunscreen materials from a shampoo composition. In EP 386,898 a cationic polygalactomannan gum derivative is used. WO 95/22311 describes the use of certain cationic polymers to increase the deposition of nonvolatile benefit agents which include silicones, fats and oils, waxes, hydrocarbons, fatty acids and fatty alcohols, lipids, vitamins and sunscreens.

U.S. Pat. No. 6,083,899 discloses fabric softener compositions that have enhanced softening benefits. The fabric softeners consist of a fabric softener active in combination with a cationic charge booster. The cationic charge boosters are suitable for use with any fabric softener active, preferably with diester and diamide quaternary ammonium (DEQA) compounds. Similar phenomena were also observed for hair care products. U.S. Pat. No. 3,980,091 discloses that the pretreatment of hair on the human head, preceding shampooing the hair with anionic type hair shampoos, and with compositions for effecting such pretreatment, to obtain highly improved manageability of the hair after shampooing and with improved fullness, comb ability and other desired properties of the hair. The pretreatment compositions utilize readily water-soluble quaternary ammonium compounds, particularly in combination with certain agents, notably polyethylenimines and N-ethanolacetamide, and desirably together with various supplemental ingredients.

Accordingly, there remains a need in the art for an efficient delivery system, to effectively deposit active ingredients onto target surfaces, such as hair, skin, and fabric and there is a need in the art for a method to provide sufficient cationic charge density onto particle surface that is needed as means to boost the overall charge density of particles thereby providing enhanced deposition of particles onto hair, skin, and fabric.

SUMMARY OF THE INVENTION

The present invention relates to a targeted controlled release composition in the form of nano spheres for targeted controlled delivery of active ingredients and sensory markers onto hair, skin, and fabric. The targeted controlled release system of the present invention is a dispersion of solid hydrophobic nano-spheres that has high cationic charge density to target and enhances the deposition of the nano-sphere onto the target site. The high cationic charge density of these nano-spheres is created by incorporating a cationic conditioning agent into the solid hydrophobic matrix of the nano-spheres or by incorporating a cationic conditioning agent into the solid hydrophobic matrix of the nano-spheres in conjunction with a cationic charge "booster" in the aqueous phase. The present invention meets the aforementioned needs in that it has been discovered that the use of combination of cationic surfactants with cationic charge booster, especially polyethyleneimine (or other polyamines, homogeneous or non-homogeneous polyamine backbones, preferably homogeneous backbones) can "boost" charge density of particles and provide enhanced deposition of particles onto hair, skin, and fabric. It has been discovered that the addition of a cationic charge boosting polymer can significantly increase the charge density of particles, to a level which enhances deposition of particles onto hair. The most effective deposition of particles onto hair is achieved by admixing cationic surfactants with a polyamine, such as polyethyleneimine, a cationic charge booster, branched, spherical, and cationic polyethyleneimine.

The present invention relates to a targeted controlled release system that effectively delivers a broad range of active ingredients and sensory markers onto hair, hair follicles, skin, and fabric as well as prolongs their release rate over an extended period of time, or provides heat triggered release of active ingredients and high impact fragrance "burst" upon blow drying the hair or ironing the fabric. The invention further relates to skin, hair, and fabric care products comprising the targeted controlled release system of the present invention.

The targeted controlled release system of the present invention can be incorporated into hair, hair follicles, skin, and fabric care products, such as shampoos, conditioners, hair styling products, hair sculpting products, lotions, creams, body wash, liquid laundry detergents, fabric softeners, and other hair, skin, and fabric care products The controlled delivery system of the present invention is a nano-sphere having a solid cationic inner core that confers several advantages as compared with conventional microspheres, liposheres, and vesicles, including high dispersibility in an aqueous medium, and a release rate for the entrapped substance that is controlled by the hydrophobic material barrier properties. There are also many advantages over other suspension-based delivery systems. Nano-spheres have increased stability as compared to emulsion-based delivery systems, including vesicles and liposomes, and are more effectively dispersed than most suspension based systems. Further, the substance to be delivered does not have to be soluble in the vehicle since it can be dispersed in the solid matrix. The nano-spheres of the present invention also have a lower risk of reaction of substance to be delivered with the vehicle than in emulsion systems because the vehicle is a solid inert material. Moreover, altering the inner solid core can manipulate the release rate of the substance from the nano-spheres. Nano-spheres are also easier to prepare than structured vehicles such as lipospheres, and are inherently more stable.

The nano-spheres of the present invention have an improved mechanism to enhance the deposition of the spheres onto hair, skin, and fabric. The highly cationic charge density characterizing the nano-spheres of the present invention, achieved by the use of cationic conditioning agents in the solid nano spheres or by using a cationic conditioning agent in solid nano-sphere in conjunction with cationic charge booster in the aqueous phase improves the deposition of these spheres onto hair, skin, and fabric and prevents them from being washed off during the rinse process. The nano-spheres of the present invention are believed to attach to the hair, skin, and fabric surfaces via entrapment, hydrophobic interactions, and complexing interaction between the cationic charge group of the spheres and the proteinaceous portion of the hair and skin and thus predispose or condition the surface of the hair and skin so that the nano-spheres will then adhere to the surface.

The nano spheres of the present invention are prepared by high shear homogenization without the need of emulsifier or surface-active materials in the aqueous phase and thus, enhance the efficacy of the encapsulation process and reduce the amount of active ingredients or sensory markers partitioning into the aqueous phase during processing of the system. The use of a surfactant in the aqueous phase during high shear homogenization has a pronounced effect on the encapsulation efficacy of active ingredients in the delivery system in the form of dispersion and emulsion. The micellar formation of the surfactants presence in the aqueous phase of these systems acts as a sink for the active ingredients encapsulated in the nano spheres and promotes partition of active ingredients from the nano sphere matrix into the water phase during processing of these systems and during the product shelf life.

In one embodiment, the present invention provides an improved controlled delivery system for hair, skin, and fabric care products, that improves the substantivity of active ingredients and sensory markers onto hair, skin, and fabric by means of bringing the spheres onto the hair, skin, and fabric through treating the hair, skin, and fabric with hair, skin, and fabric care products respectively comprising the nano-spheres of the present invention. In the industry, the term "substantivity" refers to the deposition of the active ingredients or sensory markers (i.e., fragrance) on the hair, skin, and fabric and the retention and perception of the fragrance on surfaces treated with hair, skin, and fabric care product. Spheres comprising the cationic conditioning agent either in the sphere composition, or spheres comprising cationic conditioning agent in the nano sphere solid matrix in conjunction with a cationic charge boosters in the aqueous phase (at the spheres outer surface), were observed to be highly substantive on surfaces such as skin, hair, and fabric.

The delivery system of the present invention enhances the deposition of active agents and sensory markers onto hair, skin, and fabric prolongs their release rate over an extended period of time, or release them upon heat treatment such as blow drying the hair or ironing the fabric. In addition, the release rate of the active agents is synchronized with that of a sensory marker (i.e., fragrance) to convey to the consumer the product performance.

It has been found that increasing the cationic charge density of the spheres through the use of cationic charge boosters in conjunction with cationic conditioning agents enhances the adhesion of the spheres onto hair, skin, and fabric. In addition, by incorporating cationic surface-active agents into the nano-spheres composition, the system provides improved compatibility of a wide range of active agents and sensory markers in the delivery system, and increases the substantivity of actives that are currently not substantive on hair, skin, and fabric.

Nothing in the prior art, which the applicant is aware of discloses targeted controlled release compositions of solid hydrophobic nano-spheres that have high cationic charge density to target and enhance the deposition of the nano-sphere onto the target site by incorporating a cationic conditioning agent into the solid hydrophobic matrix of the nano-spheres or by incorporating a cationic conditioning agent into the solid hydrophobic matrix of the nano-spheres in conjunction with a cationic charge "booster" in the aqueous phase, and the processing of the system does not require the use of emulsifier or surface-active materials in the aqueous phase and thus, enhance the efficacy of the encapsulation process and reduce the amount of active ingredients or sensory markers partitioning into the aqueous phase during processing of the system. The prior art of which applicant is aware does not set forth a controlled release system which synchronizes the release rate of the active ingredients with that of fragrances or sensory markers to convey the consumer the product performance.

The nano-spheres of the present invention are characterized by:

(i) protection of the active ingredients and sensory markers during storage, until needed.;

(ii) enhanced deposition of the active ingredients and sensory markers onto hair, skin, and fabric;

(iii) the release rate of the active ingredients is synchronized with that of a sensory marker;

(iv) prolong release of the active ingredients and sensory markers over an extended period of time; or (v) heat triggered release of the active ingredients and high impact fragrance "burst" upon blow drying the hair or ironing the fabric.

The invention also provides a process for producing the nano-spheres of the present invention that comprises the steps of:

a) heating the hydrophobic matrix materials to a temperature above the material melting point;
b) dissolving or dispersing the cationic conditioning agents into the melt;
c) dissolving or dispersing the active agents and/or the sensory markers into the melt;
c) dissolving or dispersing the cationic charge boosters in the aqueous phase and heating it to a temperature above the melting point of the melt;
e) mixing the hot melt with the aqueous solution to form a suspension;
f) high shear homogenization of the suspension at a temperature above the melting temperature until a homogeneous fine suspension is obtained; and
g) cooling the suspension to ambient temperature to form a fine dispersion.

It is believed that the highly substantive cationic charge booster in conjunction with the cationic conditioning agents in the spheres surface becomes associated, in use, with hair, skin, and fabric and assist in adhering the spheres onto hair, skin, and fabric through both sphere entrainment and electrostatic interactions. The highly cationic charge density of the nano-spheres, achieved by the use of cationic conditioning agents in the solid hydrophobic nano sphere matrix or by using a cationic conditioning agent in the nano sphere solid matrix in conjunction with cationic charge booster in the aqueous phase, improves the deposition of these spheres onto the hair, skin, and fabric and prevents them from being washed off during the rinse process. The nano-spheres are believed to attach to the hair and skin surfaces via a complexing interaction between the cationic charge group on the spheres and the proteinaceous portion of the hair, hair follicles or skin and thus predispose or condition the surface of the hair, hair follicle or skin so that the nano-spheres will then adhere to the surface. The hydrophobic matrix materials sustain the diffusion rate of the active ingredients and sensory markers through the spheres and enable the release of the active ingredients and sensory markers over an extended period of time, or during heat treatment such as blow drying the hair or ironing the fabric.

Hair, skin, and fabric treated with hair, skin, and fabric care products, such as shampoo, conditioners, body wash, detergents and fabric softeners, and the like, comprising the nano-spheres of the present invention were observed to exhibit high level of fragrance (high odor intensity) in both the wet and the dry state and fragrance perception on the dry hair, skin, and fabric has been observed over an extended period of time up to about one month.

The present invention also provides a cost effective controlled delivery system that improves fragrance performance from hair, skin, and fabric care products. The invention still further provides shampoos, conditioners, hair styling products, hair sculpting products, lotions, creams, body wash, liquid laundry detergents, fabric softeners, and other hair, skin, and fabric care products comprising the nano-spheres of the present invention.

DETAILED DESCRIPTION

Figure 1:
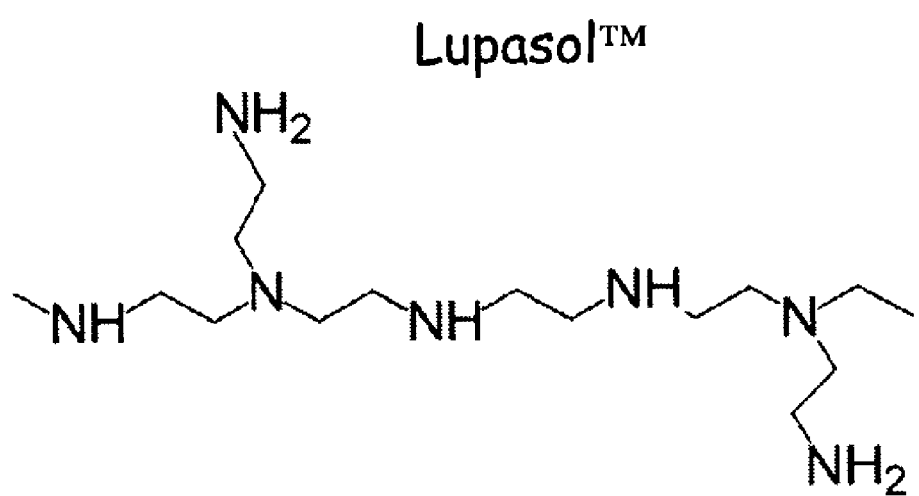
FIG. 1 is a schematic diagram of a representation of a polyvinyl amine in accordance with the teachings of the present invention.

The present invention features a method of controlling the release rate of fragrance that can be incorporated in a hair, skin, and fabric care products, over an extended period of time, or yields a high impact fragrance "burst" upon heat treatment such as blow drying the hair or ironing the fabric. Heat activation is defined as some change that is mediated by use of the composition of the invention with heat, from styling appliances such as a blow dryer, curling iron, hot curler, hot brush, hot comb, hot rollers, crimper, hair dryer, or iron. From internal testing of various appliances this average temperature can range on the "hot" setting for hair to be between 50 degree C. to 60 degree C., whereas that of fabric to be between 80 degree C. to 90 degree C. The carrier system of the present invention comprises substantially solid nano-spheres in combination with a cationic conditioning agents or a cationic conditioning agent and a cationic charge booster in the aqueous phase. The term "spheres" is intended to describe solid, substantially spherical particulates. It will be appreciated that other sphere shapes can be formed in accordance with the teachings of the present invention.

The spheres of the present invention have a predetermined sphere size. The low end of the useful size range of the spheres is limited by undue loss of volatile active agents and sensory markers from the sphere. The permeation rate of the active agents and sensory markers from the sphere is proportional to sphere size such that the smaller spheres, the faster the rate that the active agent or sensory marker is being released. The nano-spheres employed herein have an average size (diameter) range of from about 0.01 micron to about 10 microns. Preferably, the sphere size of the spheres is in the range from about 0.01 microns to about 1 micron, and spheres within this range are efficiently entrained on hair. This linear dimension for any individual sphere represents the length of the longest straight line joining two points on the surface of the sphere.

The hydrophobic core of the nano-spheres contains the active ingredients and sensory markers. The active agents and the sensory markers can be either hydrophilic or hydrophobic. Preferably the nano-spheres have an average sphere size in the range from about 0.01 microns to about 10 microns and have a melting point in the range from about 30 degrees C. to about 100 degrees C. The nano-sphere preferably comprises from about 1% to about 95% by weight hydrophobic polymers, hydrophobic copolymers, waxes, fats, or mixtures thereof, from about 0.01% to about 60% by weight cationic conditioning agents, from about 0.1% to about 70% by weight active agents, and from about 1% to about 70% by weight sensory markers. The aqueous phase can comprise from 0% to 10% by weight cationic charge booster. The nano-spheres can be incorporated into any type of hair, skin, and fabric care products.

A continuous phase of the nano-sphere dispersion formed is aqueous, and can contain the cationic charge booster and additional components such as antioxidants, preservatives, microbicides, buffers, osmoticants, cryoprotectants, and other useful additives or solutes. The additional components are present in an amount from about 1% to about 30% by weight of the aqueous dispersion.

I. Cationic Conditioning Agents

The carrier system of the present invention can comprise any of the cationic conditioning agents known in the art. The conditioning agents can include imidazolinium. Other quaternary ammonium salt hair conditioning compounds suitable for use are described in "Cationic Surfactants", Surfactant Science series, Vol. 34, edited by Richmond J. M., Marcel Dekker Inc., 1990, which are incorporated herein by reference.

Cationic conditioning agents of the present invention, are believed to attach to hair, hair follicle or skin via a complexing interaction between the cationic portion of the cationic conditioning agent and the proteinaceous portion of the hair, hair follicle, skin or fabric and thus predispose or condition the surface of the hair, hair follicle, skin or fabric so that the nano-spheres will then adhere to the surface. Surface active materials that are capable of strong bonding to the negatively charged and hydrophilic surfaces of hair, hair follicle, skin, and fabric include various straight-chain alkylammonium compounds, cyclic alkylammonium compounds, petroleum derived cationics, and polymeric cationic materials. A preferred cationic conditioning agent is Behenamidopropyl hydroxyethyl dimonium chloride and a fatty quaternary ammonium salt, available as Incroquat Behenyl HE, from Croda Inc. Parsippany, N.J.

The cationic conditioning agent can be present in a proportion of about 0.01% to about 70% by weight of the suspension, preferably about 0.1% to about 70% by weight of solid particles.

I.a.) Straight-Chain Alkylammonium Compounds

One group of cationic conditioning agents useful for enhancing the deposition of the nano-spheres of the present invention onto hair, hair follicle, skin or fabric are quaternary ammonium compounds. Quaternary ammonium salts useful herein also include dialkyldimethylammonium chlorides wherein the alkyl groups have from 12 to 22 carbon atoms. The alkyl groups can be derived from long-chain fatty acids, such as hydrogenated tallow fatty acid. Tallow fatty acid gives rise to quaternary compounds wherein the substituted groups contain predominantly from 16 to 22 carbon atoms. Examples include ditallow dimethyl ammonium chloride, ditallow dimethyl ammonium methyl sulfate, dihexadecyl dimethyl ammonium chloride, di(hydrogenated tallow)dimethyl ammonium chloride, dioctadecyl dimethyl ammonium chloride, dieicosyl dimethyl ammonium chloride, didocosyl dimethyl ammonium chloride, di(hydrogenated tallow)dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl)dimethyl ammonium chloride, and stearyl dimethyl benzyl ammonium chloride. Preferred quaternary ammonium salts useful herein include ditallow dimethyl ammonium chloride, dicetyl dimethyl ammonium chloride, stearyl dimethyl benzyl ammonium chloride, cetyl trimethyl ammonium chloride, tricetyl methyl ammonium chloride, and mixtures thereof. Di(hydrogenated tallow)dimethyl ammonium chloride (Quaternium-18) is a particularly preferred quaternary ammonium salt, and is available from the Sherex Chemical Company, Inc. as Adogen® 442 and Adogen® 442-100P.

Salts of primary, secondary and tertiary fatty amines can also be used as cationic conditioning agents. The alkyl groups of such amines preferably have from 12 to 22 carbon atoms, and can be substituted or unsubstituted. Secondary and tertiary amines are preferred; and tertiary amines are particularly preferred. Examples of useful amines include stearamido propyl dimethyl amine, diethyl amino ethyl stearamine, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Examples include stearylamine hydrochloride, soyamine chloride, stearylamine formate, N-tallowpropane diamine dichloride and stearamidopropyl dimethylamine citrate.

Suitable conditioning agents are quaternary ammonium salts. Quaternary ammonium salts include dialkyldimethylammonium chlorides, wherein the alkyl groups have from 12 to 22 carbon atoms. These alkyl groups may be derived from long-chain fatty acids, such as hydrogenated tallow fatty acid. Tallow fatty acid gives rise to quaternary compounds wherein the substituted groups predominantly contain from 16 to 18 carbon atoms. Examples of quaternary ammonium salts include: di(hydrogenated)tallow dimethyl ammonium chloride; dicetyl dimethyl ammonium chloride; tricetyl methyl ammonium chloride; cetyl trimethyl ammonium chloride; stearyl dimethyl benzyl ammonium chloride; and mixtures thereof. Most preferred is dicetyl dimethyl ammonium chloride.

Other suitable conditioning agents are: behenalkonium chloride; behentrimonium chloride; behenalkonium methosulfate; behentrimonium methosulfate; behenamidopropylamine oxide; behenopropyl dimethylamine; behenamidopropyl dimethylamine; behenamidopropyl dimethylamine behenate; behenamidopropyl ethyldimonium ethosulfate; behenamidopropyl PG-dimonium chloride; behenamine; and behenamidopropyl hydroxyethyl dimonium chloride.

I.b.) Cyclic Alkylammonium Compounds

Another preferred group of compounds of cationic conditioning agents useful for enhancing deposition of nano-spheres onto the hair, hair follicles, skin, and fabric include a class of surface-active quaternary ammonium compounds in which the nitrogen atom carrying the cationic charge is part of a heterocyclic ring. Suitable compounds, for example, are as follows: laurylpyridinium chloride or bromide; tetradecylpyridinium bromide; and cetylpyridinium halide, wherein the halide is chloride, bromide or fluoride.

I.c.) Petroleum Derived Cationic Compounds

Typical basic amines useful for the present invention are derived from petroleum-based raw materials such as olefins, paraffins, and aromatic hydrocarbons and include compounds with at least one aliphatic carbon chain containing six or more carbon atoms attached to the nitrogen. Amine salts, diamines, amidoamines, alkoxylated amines, and their respective quaternary salts are suitable for the present invention. Suitable compounds of this type include tallow or coco alkyl substituted 1,3-propylene diamines sold by Witco under the names of "Adogen" and "Emcol" and similar diamines sold by Akzo under the name "Duomeen" and polyethenoxy derivatives sold by Akzo under the names of "Ethomeen" and "Ethoduomeens".

I.d.) Cationic Polymers

Cationic polymers suitable for use in the present invention are selected from the group of polyquaternium 32, polyquaternium 3, cocodimonium hydroxypropyl hydrolyzed collagen, cocodimonium hydroxypropyl hydrolyzed hair keratin, cocodimonium hydroxypropyl hydrolyzed hair keratin, cocodimonium hydroxypropyl hydrolyzed keratin, cocodimonium hydroxypropyl hydrolyzed wheat protein, cocodimonium hydroxypropyl oxyethyl cellulose, guar hydroxypropyltrimonium chloride, lauryldimonium hydroxypropyl hydrolyzed collagen, lauryldimonium hydroxypropyl hydrolyzed wheat protein, lauryldimonium hydroxypropyl oxyethyl cellulose, polyquaternium 4, polyquaternium 10, polyquaternium 24, steardimonium hydroxyethyl cellulose, steardimonium hydroxypropyl hydrolyzed collagen, steardimonium hydroxypropyl hydrolyzed wheat protein, steardimonium hydroxypropyl oxyethyl cellulose, steardimonium hydroxyethyl hydrolyzed collagen, polymethacrylamidopropyl trimonium chloride, polyquaternium 2, polyquaternium 6, polyquaternium 7, polyquaternium 11, polyquaternium 16, polyquaternium 17, polyquaternium 18, polyquaternium 22, polyquaterium 24, polyquaternium 27, polyquaternium 28, polyquaternium 31, polyquaternium 39, polyquaternium 41, polyquaternium 42, quaternium 80, and quaternized hydrolyzed wheatiprotein/dimethicone phosphocopolyol copolymer. The preferred cationic conditioning agent are polyquaterium-24 available under the name Quatrisoft® polymer LM-200, from Amerchol Corporation.

Also suitable, for the purpose of this invention, are cationic derivatives of polysaccharides such as dextran, starch or cellulose, for example, diethylaminoethyl cellulose ("DEAE-cellulose"). Further examples of suitable materials are the cationic guar derivatives such as those sold under the trade name JAGUAR® by Celanese-Hall.

A further preferred group of compounds, which comprises a class of water-insoluble polymers, having nitrogen atoms in their molecules, are quaternary polymers of quaternary ammonium type, betaine type, pyridylpyridinium type or vinylpyridinium-type. Examples are as follows poly(vinylbenzylmethyllaurylammonium chloride); poly(vinyl-benzylstearylbetaine); poly(vinyl-benzyllaurylpyridylpyridinium chloride); poly(vinyl-benzylcetylammonylhexyl ether) and quaternized polyoxyethyleneated long chain amines, with the general formula $RN(CH_3)[(C_2H_4O)_xH]_2(+)$ A(−), where A(−) is generally chloride or fluoride, x is a number from 1 to 20, and R is $C_{8-22}$-alkyl.

In a preferred embodiment, the cationic conditioning agent is A preferred cationic conditioning agent is behenamidopropyl hydroxyethyl dimonium chloride and a fatty quaternary ammonium salt, available as Incroquat Behenyl HE, from Croda Inc. Parsippany, N.J.: The cationic conditioning agent can be present in a proportion of about 0.01% to about 70% by weight of the suspension, preferably about 0.1% to about 70% by weight.

II. Cationic Charge Boosters

The controlled delivery system of the present invention may comprises a cationic charge booster in the aqueous phase of the dispersion. Suitable cationic charge boosters are described in U.S. Pat. No. 6,083,899 hereby incorporated by reference into this application. The preferred cationic charge boosters of the present invention are described herein below.

II.a. Quaternary Ammonium Compounds

A preferred composition of the present invention comprises preferably from about 0% to about 10%, more preferably from about 0% to about 5% by weight, of a cationic charge booster having the formula:

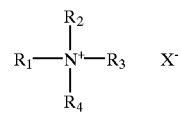

wherein $R_1$, $R_2$, $R_3$, and $R_4$ are each independently $C_1$–$C_{22}$ alkyl, $C_3$–$C_{22}$ alkenyl, $R_5$——Q——$(CH_2)_m$——, wherein $R_s$ is $C_1$–$C_{22}$ alkyl, and mixtures thereof, m is from 1 to about 6; X is an anion. Preferably $R_1$ is $C_6$–$C_{22}$ alkyl, $C_6$–$C_{22}$ alkenyl, and mixtures thereof, more preferably $R_1$ $C_{11}$–$C_{18}$ alkyl, $C_{11}$–$C_{18}$ alkenyl, and mixtures thereof; $R_2$, $R_3$, and $R_4$ are each preferably $C_1$–$C_4$ alkyl, more preferably each $R_2$, $R_3$, and $R_4$ are methyl.

Alternatively, $R_1$ can be a $R_5$——Q——$(CH_2)_m$—— moiety wherein $R_5$ is an alkyl or alkenyl moiety having from 1 to 22 carbon atoms, preferably the alkyl or alkenyl moiety when taken together with the Q unit is an acyl unit. For example Q can be derived from a source of triglyceride selected from tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

An example of a cationic charge booster comprising a $R_5$——Q——$(CH_2)_m$—— moiety has the formula:

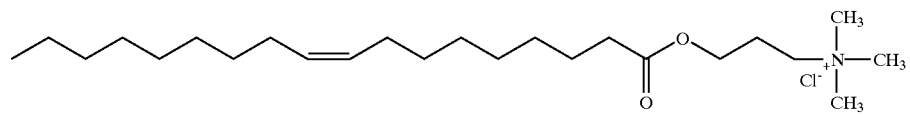

wherein $R_5$——Q—— represents oleoyl units and m is equal to 2.

Preferably X is a softener compatible anion, such as the anion of a strong acid. For example, X can be chloride, bromide, methylsulfate, ethylsulfate, sulfate, nitrate and mixtures thereof. More preferably X is chloride and methyl sulfate.

II.b. Polyvinyl Amines

A preferred composition according to the present invention contains from about 0% to about 10%, more preferably from about 0% to about 5% by weight, of one or more polyvinyl amines charge boosters having the formula

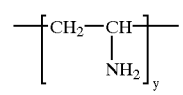

wherein y is from about 3 to about 10,000, preferably from about 10 to about 5,000, more preferably from about 20 to about 500. Polyvinyl amines suitable for use in the present invention are available from BASF under the name Lupasol® LU 321. Lupasol™ has very strong affinity for anions and polar materials and has very good binding properties; ionic bonding 10–30 Kcal/mol, hydrogen bonding 4–6 Kcal/mol, van der Waals bonding 0.5–2 Kcal/mol. An example of the polyvinyl amine referred to as Lupasol™ is shown in FIG. 1. The greater number of amine moieties per unit weight on the polyvinyl amines provides preferred substantial charge density.

II.c. Polyalkyleneimines

A preferred composition of the present invention comprises from about 0% to about 10%, more preferably from about 0% to about 5% by weight, of a polyalkyleneimine charge booster having the formula:

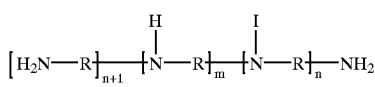

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary:secondary:tertary amine moieties of ——RNH$_2$, ——RNH, and ——RN moieties, is 1:2:1. R can be $C_2$–$C_8$ alkylene, $C_3$–$C_8$ alkyl substituted alkylene, and mixtures thereof. Preferably R is ethylene, 1,2-propylene, 1,3-propylene, and mixtures thereof, and more preferably ethylene. R radicals serve to connect the amine nitrogens of the backbone.

Optionally, one or more of the polyvinyl amine backbone ——NH$_2$ unit hydrogens can be substituted by an alkyleneoxy unit having the formula:

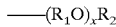

wherein $R_1$ is $C_2$–$C_4$ alkylene; $R_2$ is hydrogen, $C_1$–$C_4$ alkyl, and mixtures thereof; and x is from 1 to 50. In one embodiment or the present invention the polyvinyl amine is reacted first with a substrate which places a 2-propyleneoxy unit directly on the nitrogen followed by reaction of one or more moles of ethylene oxide to form a unit having the general formula:

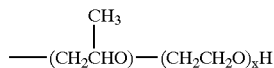

wherein x has the value of from 1 to about 50. Substitutions such as the above are represented by the abbreviated formula PO——EO——. However, more than one propyleneoxy unit can be incorporated into the alkyleneoxy substituent.

The preferred polyamine cationic charge boosters of the present invention comprise backbones wherein less than about 50% of the R groups comprise more than 3 carbon atoms. The use of two and three carbon spacers as R moieties between nitrogen atoms in the backbone is advantageous for controlling the charge booster properties of the molecules. More preferred embodiments of the present invention comprise less than about 25% moieties having more than 3 carbon atoms. Yet more preferred backbones comprise less than about 10% moieties having more than 3 carbon atoms. Most preferred backbones comprise about 100% ethylene moieties.

The cationic charge boosting polyamines of the present invention comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

However, not all of the suitable charge booster agents belonging to this category of polyamine comprise the above described polyamines. Other polyamines that comprise the backbone of the compounds of the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™ PR8515, having an average molecular weight of 1,800, Lupasol™ Waterfree; Lupasol™ P, Lupasol™ PR971L; Lupasol™ PL; Lupasol™ SKA. Ethoxylated polyethyleneimines suitable for use in the present invention are available from BASF under the name Lupasol™ SC®-61B. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly nonamines, the cogenerically derived mixture does not appear to separate by distillation and can include other materials such as cyclic amines and particularly piperazines.

II.d. Poly-Quaternary Ammonium Compounds

A preferred composition of the present invention comprises from about 0% to about 10%, more preferably from about 0% to about 5% by weight, of a cationic charge booster having the formula:

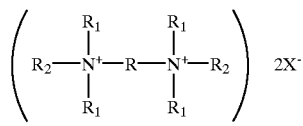

wherein R is substituted or unsubstituted $C_2$–$C_{12}$ alkylene, substituted or unsubstituted $C_2$–$C_{12}$ hydroxyalkylene; each $R_1$ is independently $C_1$–$C_4$ alkyl, each $R_2$ is independently $C_1$–$C_{22}$ alkyl, $C_3$–$C_{22}$ alkenyl, $R_5$——Q——$(CH_2)_m$——, wherein $R_5$ is $C_1$–$C_{22}$ alkyl, $C_3$–$C_{22}$ alkenyl, and mixtures thereof; m is from 1 to about 6; Q is a carbonyl unit as described above and mixtures thereof; X is an anion.

Preferably R is ethylene and $R_1$ is preferably methyl or ethyl, more preferably methyl. Preferably at least one $R_2$ is $C_1$–$C_4$ alkyl, more preferably methyl. Most preferably at least one $R_2$ is $C_{11}$–$C_{22}$ alkyl, $C_{11}$–$C_{22}$ alkenyl, and mixtures thereof.

Alternatively $R_2$ is a $R_5$——Q——$(CH_2)_m$—— moiety wherein $R_5$ is an alkyl moiety having from 1 to 22 carbon atoms, preferably the alkyl moiety when taken together with the Q unit is an acyl unit derived from a source of triglyceride selected from the group consisting of tallow, partially hydrogenated tallow, lard, partially hydrogenated lard, vegetable oils, partially hydrogenated vegetable oils, such as, canola oil, safflower oil, peanut oil, sunflower oil, corn oil, soybean oil, tall oil, rice bran oil, and the like and mixtures thereof.

An example of a fabric softener cationic booster comprising a $R_5$——Q——$(CH_2)_m$—— moiety has the formula:

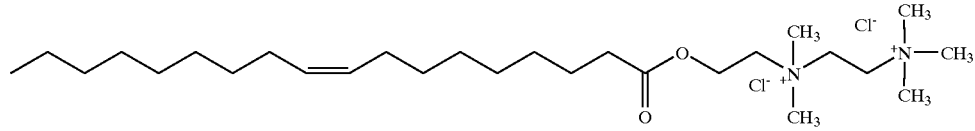

wherein $R_1$ is methyl, one of the $R_2$ units is methyl and the other of the $R_2$ unit is $R_5$——Q—— $(CH_2)_m$—— wherein $R_5$——Q—— is an oleoyl unit and m is equal to 2. X is a softener compatible anion, such as an anion of a strong acid. For example, X can be chloride, bromide, methylsulfate, ethylsulfate, sulfate, nitrate and mixtures thereof. More preferably chloride and methyl sulfate.

III. Matrix Materials

The matrix materials for forming the spheres of the carrier system of the present invention comprise any substantially water-insoluble polymers, copolymers, waxes, fats, and mixtures thereof with a melting point range between about 30 degrees C. and about 100 degrees C., that are compatible with and miscible with the active agents or sensory markers composition used in the present invention and harmless or beneficial to the hair, hair follicles, skin, and fabric when dispersed and melted on to them.

Examples of hydrophobic materials include natural, regenerated, or synthetic waxes including animal waxes such as beeswax, lanolin and shellac wax, vegetable waxes such as carnauba, candelilla, sugar cane, rice bran, and bayberry wax, mineral waxes such as petroleum waxes including paraffin and microcrystalline wax, and mixtures thereof. Other hydrophobic materials which can be used in the present invention include wax and silicon copolymers, such as candelilla wax and silicone copolymer, ozokrite wax and silicon copolymers, beeswax and silicon copolymers, and the like. Other hydrophobic compounds which can be used in the present invention include: fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol, solid hydrogenated castor and vegetable oils, hard paraffins, hard fats, and mixtures thereof. Other hydrophobic compounds which can be used, include triglycerides, preferably of at least food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–C18), denoted medium chain triglycerides (MCT). The fatty acid moieties of such triglycerides can be unsaturated or polyunsaturated and mixtures of triglycerides having various fatty acid material. The nano sphere matrix can comprise a single hydrophobic material or a mixture of a plurality of materials. Other hydrophobic materials that are known to those skilled in the art and suitable materials as described in "Industrial Waxes," Vol. I and II, by Bennett F.A.I.C., published by Chemical Publishing Company Inc., 1975 and Martindale, "The Extra Pharmacopoeia", The Pharmaceutical Press, $28^{th}$. Edition pp. 1063–1072, 1982 can be used in the present invention.

Other hydrophobic compounds which can be used in the present invention include synthetic polymers, such as alkylated polyvinylpyrrolidines, the Ganex® copolymer series, and ProLipids® 151 (commercially available from the ISP Company), Purester® series of materials (especially Purester® 24 and Purester® 34, vegetable derived esters produced from naturally derived fatty alcohol & methyl ester feedstocks which are non-GMO vegetable based renewable resources, commercially available from Strahl & Pitsch Inc. of West Babylon, N.Y.)

Examples of other suitable hydrophobic polymers and copolymer for use as the matrix material include polyethylene homopolymers A——C® 1702; A-C® 617, A-C® 617A, and A-C® 15, commercially available from Allied Signal Inc.; PERFORMALENE™ polyethylene homopolymer series commercially available from New Phase Technologies; PERFORMACOL™ linear primary alcohols series commercially available from New Phase Technologies; PERFORMACID™ linear saturated carboxylic acid series commercially available from New Phase Technologies; PERFORMA V™ polymer series commercially available from New Phase Technologies; ETHYLENE-ACRYLIC ACID COPOLYMERS A-C® 540, A-C® 540A, and A-C® 580 commercially available from Allied Signal Inc.; polyamides having a molecular weight in the range of from about 6,000 up to about 12,000, for example, MAC-ROMELT™ 6030 manufactured by the Henkel Ag. of Dusseldorf, Germany; VERSALON™ 1135 polyamide polymer available commercially from General Mills, Inc It is preferred that the nano-spheres of the present invention have a melting point in the range from about 30 degrees C. to about 100 degrees C., preferably from about 40 degrees C. to about 90 degrees C. The melting point of the spheres is usually a function of the carrier matrix employed. Accordingly, preferred matrix materials have a melting point in the range of about 40 degrees C. to about 80 degrees C., preferably from about 50 degrees C. to about 70 degrees C. It should be understood that it is the melting point of the sphere rather than of the carrier matrix that is important for use of the carrier system of the present invention.

Considerations in the selection of the matrix material include good barrier properties to the active agents and the fragrance ingredients, low toxicity and irritancy, stability, and high loading capacity for the active agents of interest.

V. Active Agents

The active agents can be cosmetic, dermatological, and pharmaceutical active agents. Suitable active agents include ceramides, vitamins, antioxidants, free radical scavengers, moisturizing agents, anti-seborrhoeic agents, anti-UV agents, keratolytic agents, anti-inflammatory agents, refreshing agents, melanoregulators, liporegulators, antiseborrhoeic agents, anti-ageing agents, keratolytic agents, antibacterial agents, anti-dandruff agents, agents for combating hair loss, hair dyes, hair bleaches, reducing agents for permanent waves, hair conditioners and nutrients, cicatrizing agents, vascular protectors, antibacterial agents, anti fungal agents, skin conditioners, immunomodulators, nutrients and essential oils, retinoids, anesthetics, surfactants, emulsifiers, stabilizers, preservatives, antiseptics, emollients, lubricants, humectants, analgesics, enzymes, pigments, dyes, hydroxy acids, such as, alpha hydroxy acids, and beta hydroxy acids, emollients, medications, antibiotics, repellants, attractants such as, pheromones, fragrances, sensory markers such as cooling agents of menthol derivatives, hyaluronic acid and its salts, elastin, hydrolysates, primrose oil, jojoba oil, epidermal growth factor, soybean saponins, mucopolysaccharides, ironing aids such as silicones; anti-shrinkage agents; anti-wrinkle agents; bleaching agents, fabric crisping agents; spotting agents; germicides; fungicides; stabilizers preservatives; bactericides which can be effective to protect the composition or to treat fabrics; and mixtures thereof. The fragrance can have a calculated logP (ClogP) in the range of about 1 to about 8.

Drugs

Suitable drugs which can be administered in the delivery system of the present invention include but are in no way limited to anti-bacterial agents such as thimerosal, chloramine, boric acid, phenol, iodoform, chlorhexidine and other oral antiseptics, beta-lactam antibiotics, for example cefoxitin, n-formamidoyl thienamycin and other thienamycin derivatives, tetracyclines, chloramphenicol, neomycin, gramicidin, kanamycin, amikacin, sismicin and tobramycin; anti-inflammatory steroids such as cortisone, hydrocortisone, beta-methasone, dexamethasone, fluocortolone, prednisolone, triamcinolone and the like. The biologically active ingredient my also be one or more antibiotics, such as penicillin, polymyxin B, vancomycin, kanamycin, erythromycin, niddamycin, metronidazole, spiramycin and tetracycline.

Sensory Markers

The present invention can include sensory markers such as fragrances and cooling agents such as menthol derivatives. Preferably the sensory markers are synchronized with the release of the active agents to convey to the consumer the product performance, provide long lasting odor and signal that a new application of the product is needed.

The fragrance ingredients and compositions of this invention can be conventional ones known in the art. Selection of any perfume component, or amount of perfume, is based on functional and aesthetic considerations. Typical examples of usable fragrance and flavor compounds discussed hereinafter, along with their odor characters, and their physical and chemical properties, are described in "Perfume and Flavor Chemicals (Aroma Chemicals)", Steffen Arctander, published by the author, 1969, and in "Common Fragrance and flavor Materials—Preparation, Properties and Uses", Kurt Bauer and Dorotea Garbe, published by VCH Verlagsgesellschaft mbH, 1985, incorporated herein as reference.

Preservatives

Preservatives can be incorporated into the present invention to protect against the growth of potentially harmful microorganisms. While it is in the aqueous phase that microorganisms tend to grow, microorganisms can also reside in the anhydrous or oil phase. As such, preservatives, which have solubility in both water and oil, are preferably employed in the present compositions. Suitable traditional preservatives for compositions of this invention are alkyl esters of parahydroxybenzoic acid. Other preservatives, which can be used include hydantoin derivatives, propionate salts, and a variety of quaternary ammonium compounds.

Particularly preferred preservatives are methylparaben, imidazolidinyl urea, sodium dehydroacetate, propylparaben, trisodium ethylenediamine tetraacetate (EDTA), and benzyl alcohol. The preservative can be selected to avoid possible incompatibilities between the preservative and other ingredients. Preservatives are preferably employed in amounts ranging from about 0.01% to about 2% by weight of the composition. Other preservatives known in the art can be used in the present invention.

VI. Processing Method

The sphere-making procedures described generally in Nixon (ed.), Microencapsulation, pp. 13–38 (Marcel Dekker, Inc. 1976); Muller, Colloidal Carriers for Controlled Drug Delivery and Targeting, pp. 175–202 (CRC Press 1991); Shaw (ed.), Lipoproteins as Carriers of Pharmacological Agents, pp. 97–139 (Marcel Dekker, Inc. 1991); and Benita (ed.), Microencapsulation—Methods and Industrial applications, pp. 183–258 (Marcel Dekker, Inc. 1996).

The process for producing the nano-spheres comprises the steps of:

a) heating the hydrophobic matrix materials to a temperature above the material melting point;

d) dissolving or dispersing the cationic conditioning agents into the melt;

e) dissolving or dispersing the active agents and/or the sensory markers into the melt;

c) dissolving or dispersing the cationic charge boosters in the aqueous phase and heating it to a temperature above the melting point of the melt;

e) mixing the hot melt with the aqueous solution to form a suspension;

f) high shear homogenization of the suspension at a temperature above the melting temperature until a homogeneous fine suspension is obtained; and g) cooling the suspension to ambient temperature to form a fine dispersion.

The melt phase is dispersed into the aqueous phase by agitation, such as with an ultrasonic processor, high pressure homogenizer, colloid mill, or high sheer mixer until small, fairly uniform size spheres are formed. The dispersion is then cooled to at least room temperature to form the final suspension of hydrophobic phase spheres within the continuous aqueous phase.

The fairly uniform spheres formed within the aqueous phase should be less than about 2 microns, preferably have number average diameters of less than about 1 micron, more preferably have number average diameters of less than about 0.5 microns, and most preferably have number average diameters of between about 0.01 and about 0.5 microns, with about 0.1 to about 1 microns being particularly preferred.

The method of preparation of nano-spheres described herein is simple and is characterized by high loading, reproducibility, versatility, and stability. The method is further illustrated in the non-limiting examples.

The active agents and sensory markers that are dissolved within in the nano-spheres can be released by molecular diffusion at a rate according to Fick's second law of diffusion described in "Diffusion in Polymers", Crank J. and Park G. S., Academic Press, New-York, 1969; "Barriers Polymers and Structures", Edited by Koros W. J., ACS Series, Washington D.C., 1990; "Polymer Permeability", Edited by J. Comyn, Elsevier Applied Science publishers, 1985 pp. 217–267; incorporated herein as references:

$$\frac{\partial C}{\partial t} = \frac{\partial}{\partial X}\left(D\frac{\partial C}{\partial X}\right) = D\frac{\partial^2 C}{\partial X^2}$$

where:
D=diffusion coefficient
C=concentration of the diffusing molecule
X=direction of diffusion
t=time Higuchi has developed equations for spherical monolithic devices having homogenous matrices (Higuchi T., J. Pharm. Sci., 52, 1145, 1963). The theoretical early and late time approximation of the release rate of the active ingredients dissolved in the hydrophobic matrix of the nano spheres can be calculated from the following equations:

Early lime approximation $(m_t/m_\infty) < 0.4$ $$\frac{M_t}{M_\infty} = 6\left[\frac{Dt}{r^2\pi}\right]^{1/2} - \frac{3Dt}{r^2}$$

Late time approximation $(m_t/m_\infty) > 0.6$ $$\frac{M_t}{M_\infty} = 1 - \frac{6}{\pi^2}\exp\left[\frac{-\pi^2 Dt}{r^2}\right]$$

Where;
r—the radius of the cylinder
$m_\infty$—the amount of active released from the controlled release system after infinite time
$m_t$—the amount of active released from the controlled release system after time t
D—the diffusion coefficient of the fragrance or aroma chemical in the polymer Brophy and Deasy (Brophy M. and Deasy p .B., Int. J. Pharm., 37, 41, 1987) developed an equation based on the pseudo steady state approximation of Higuchi. The equation derived describes the release of a dispersed solute from a rigid sphere matrix where there is no swelling or erosion of the matrix.

$$M_t = A[DCs(2Co - Cs)t]^{1/2} - \frac{4}{9}8\pi r \, DCs\frac{3Co - 2Cs}{2Co - Cs}t$$

Where:
Co is active concentration in the microspheres
Cs is the active solubility (the saturation concentration)
r is the radius of the sphere The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and claims, are by weight and are approximations unless otherwise stated.

Preparation of Nano Spheres Fragrance Delivery Systems

EXAMPLE 1

The fragrance used in the following examples is a fragrance composition that is not substantive on hair when used as neat oil. The fragrance composition used is as follows:

| Perfume Composition | Component (% Wt.) |
| --- | --- |
| Geraniol | 30.0 |
| Dihydro Myrcenol | 20.0 |
| Phenyl Ethyl Alcohol | 5.0 |
| Linalool | 25.0 |
| Tetrahydro Linalyl Acetate | 20.0 |

The nano-spheres had the following composition; Incroquat Behenyl HE, behenamidopropyl hydroxyethyl dimonium chloride (a fatty quaternary ammonium salt, commercially available from Croda) was used as cationic conditioning agent and LUPASOL™ PR815, a polyethyleneimine having an average molecular weight of 1800 (commercially available from BASF Corporation) was used as a cationic charge booster. The hydrophobic polymer was candelilla/silicon copolymer (commercially available from Strahl & Pitsch Inc.) The suspension is homogenized using an APV, Rannie 2000 high pressure homogenizer. The resulting formulation is:
64.9% water
20% candelilla/silicon copolymer
10% Fragrance
5% Incroquat Behenyl HE
0.1% LUPASOL™ PR815

200 grams of candelilla/silicon copolymer is placed in an oven at 120 degrees C. and allowed to melt. 649 grams of deionized water is placed into one gallon vessel of the homogenizer, that fitted with a all-purpose silicon rubber heater (Cole-Palmer Instrument Company). 1 grams of LUPASOL™ PR815 is added to the water and the aqueous solution is heated to 90 degrees C. while mixing it with a propeller mixer. The candelilla/silicon copolymer melt is removed from the oven, 50 grams of Incroquat Behenyl HE and 100 grams fragrance are mixed into the candelilla/silicon copolymer melt by hand with a glass rod. The melt mixture is than poured into the vessel containing aqueous solution and the emulsion is homogenized at 20,000 psi. The dispersion is cooled to ambient temperature by passing it through a tube-in-tube heat exchanger (Model 00413, Exergy Inc. Hanson Mass.).

EXAMPLE 2

The nano-spheres had the following composition; Incroquat Behenyl HE, behenamidopropyl hydroxyethyl dimonium chloride (a fatty quaternary ammonium salt, commercially available from Croda) was used as cationic conditioning agent. The hydrophobic polymer was polyethylene homo-polymer (commercially available from New Phase Technologies.) The suspension is homogenized using an APV, Rannie 2000 High Pressure Homogenizer. The resulting formulation is:

60% water;
10% fragrance;
10% Incroquat Behenyl HE
20% polyethylene 200 grams of polyethylene polymer is placed in an oven at 120 degrees C. and allowed to melt. 600 grams of deionized water is placed into one gallon vessel of the homogenizer, that fitted with a all-purpose silicon rubber heater (Cole-Palmer Instrument Company). The water and the aqueous solution is heated to 95 degrees C. The polyethylene polymer is removed from the oven, 100 grams of Incroquat Behenyl HE and 100 grams of fragrance are mixed into the polyethylene polymer by hand with a glass rod. The melt mixture is than poured into the vessel containing water and the emulsion is homogenized at 20,000 psi. The dispersion is cooled to ambient temperature by passing it through a tube-in-tube heat exchanger (Model 00413, Exergy Inc. Hanson Mass.).

Preparation of Nano Spheres Delivery Systems for Skin

EXAMPLE 3

The nano-spheres had the following composition; Incroquat Behenyl HE, behenamidopropyl hydroxyethyl dimonium chloride (a fatty quaternary ammonium salt, commercially available from Croda) was used as cationic conditioning agent. The hydrophobic polymer was polyethylene homo-polymer, PERFORMA V™ 216 (commercially available from New Phase Technologies.) The suspension is homogenized using an APV, Rannie 2000 High Pressure Homogenizer. The resulting formulation is:

60% water;
10% Retinol (commercially available from BASF)
10% Incroquat Behenyl HE
20% PERFORMA V™ 216

200 grams of polyethylene polymer is placed in an oven at 120 degrees C. and allowed to melt. 600 grams of deionized water is placed into one gallon vessel of the homogenizer, that fitted with a all-purpose silicon rubber heater (Cole-Palmer Instrument Company). The water and the aqueous solution is heated to 95 degrees C. The polyethylene polymer is removed from the oven, 100 grams of Incroquat Behenyl HE and 100 grams of Retinol are mixed into the polyethylene polymer by hand with a glass rod. The melt mixture is than poured into the vessel containing water and the emulsion is homogenized at 20,000 psi. The dispersion is cooled to ambient temperature by passing it through a tube-in-tube heat exchanger (Model 00413, Exergy Inc. Hanson Mass.).

EXAMPLE 4

The nano-spheres had the following composition; incroquat behenyl HE, behenamidopropyl hydroxyethyl dimonium chloride (a fatty quaternary ammonium salt, commercially available from Croda) was used as cationic conditioning agent. The hydrophobic polymer was polyethylene homo-polymer (commercially available from New Phase Technologies.) The suspension is homogenized using an APV, Rannie 2000 high pressure homogenizer. The resulting formulation is:

65% water;
10% Vitamin E
5% Incroquat Behenyl HE 20% Ganex V™ 660

200 grams of Ganex V™ 660 polymer is placed in an oven at 100 degrees C. and allowed to melt. 650 grams of deionized water is placed into one gallon vessel of the homogenizer, that fitted with a all-purpose silicon rubber heater (Cole-Palmer Instrument Company). The water and the aqueous solution is heated to 95 degrees C. The polyethylene polymer is removed from the oven, 50 grams of incroquat behenyl HE and 100 grams vitamin E are mixed into the Ganex V™ 660 polymer by hand with a glass rod. The melt mixture is than poured into the vessel containing water and the emulsion is homogenized at 20,000 psi. The dispersion is cooled to ambient temperature by passing it through a tube-in-tube heat exchanger (Model 00413, Exergy Inc. Hanson Mass.).

Test Methods for Fabric Care Products

Twenty cotton towels having the following dimensions 14"×17" were used for evaluating the performance of the fragrance carrier spheres of the present invention. Ten of the towels were 100% cotton and ten were composed of a mixture of 65% polyester and 35% cotton. The fabric was laundered in an American washing machine Kenmore™ 90 series.

Wash Conditions:
Fabric Load: 20 towels
Laundry detergent sample size: 100 grams
Fabric softener sample size: 30 grams
Dosing into the machine: Laundry detergent was dosed directly into the machine Fabric softener was placed in the dispenser
Water level: Small Load
Water temperature: Cold/Cold
Cycle: Short cycle
Water temperature: Cold/Cold
Rinse options: One rinse cycle
Speeds: Heavy duty The laundered fabric was line dried overnight in a fragrance free room. The dry fabric was folded into two and placed into an aluminum tray, approximately 5 cm deep, covered with a perforated aluminum sheet, in order to keep it out of view, up to the moment of the sniff-test. The sniff-test was performed on the dry laundered fabric in a "pre-ventilated" room by ten graders, 24 hours following wash. The laundered fabric was then covered with a perforated aluminum sheet, and was evaluated again after one week and two weeks by a sniff-test method.

Odor perception is, by its nature, a very subjective determination. According to the procedure, the samples to be tested are provided to a panel of ten odor specialists who independently rank odor intensity of the dry laundered fabric using a scale of 1 (no perceived odor) to 10 (high odor intensity). Samples yielding an odor ranking below about 2 possess an odor which would hardly be noticed by the general public.

Incorporation of the Nano Spheres in Fabric Care Products

EXAMPLE 5

The performance of a liquid laundry detergent product comprising the fragrance carrier system of Example 1 (i.e., the ability to increase fragrance deposition onto fabric, as well as the ability to prolong fragrance release from the dry laundered fabric over an extended period of time, or yield a high impact fragrance "burst" upon ironing the fabric) was evaluated and compared to the performance of the same detergent comprising the neat fragrance, at the same fragrance level. The unfragranced liquid laundry detergent base was a commercial TIDE™ FREE liquid laundry detergent available from Procter & Gamble Company of Cincinnati, Ohio that is fragrance free.

The laundry samples were prepared at a 1% effective fragrance concentration using the fragrance described in Example 1. The control sample was prepared by weighting into a jar 1 gram of the neat fragrance and 99 grams of the TIDE™ FREE unfragranced and the resulting mixture was mixed for about one hour. The liquid laundry detergent comprising the fragrance spheres of the present invention was prepared by weighting into a jar 3.3 grams of the fragrance spheres of example 2 and 96.7 grams of the TIDE™ FREE unfragranced liquid laundry detergent base and the resulting mixture was mixed for about one hour.

Twenty towels were placed in the washing machine (10 of the towels used were 100% cotton and the other 10 towels were 65% polyester and 35% cotton) with 100 grams of powder laundry detergent dosed directly into the washing machine.

The following washing machine cycle was used:
Fabric Load: 20 towels
Laundry detergent sample size: 100 grams
Dosing into the machine: Laundry detergent was dosed directly into the machine
Water level: Small Load
Water temperature: Cold/Cold
Cycle: Short cycle
Water temperature: Cold/Cold
Rinse options: One rinse cycle
Speeds: Heavy duty Cloth samples were line-dried for 24 hours and then evaluated at four stages: immediately after drying (24 hours following wash); upon ironing 24 hours following wash; at one week after drying; and at two weeks after drying. The dry fabric was folded into two and placed into an aluminum tray, approximately 5 cm deep, covered with a perforated aluminum sheet, between the evaluation stages, up to the moment of the sniff-test. The sniff-test was performed on the dry laundered fabric in a "pre-ventilated" room by ten graders, and test results are presented below:

|  | 24 Hours Following Wash | |
| --- | --- | --- |
| Sample | Dry Fabric | Upon Ironing |
| Neat Fragrance (Control) | 3 | 4 |
| Encapsulated Fragrance (Example 1) | 6 | 8 |

Test results indicate that the cloth samples washed with the encapsulated fragrance of Example 1 are significantly more intense than the control samples washed with the neat fragrance immediately after drying (24 hours following wash).

A significant increase in fragrance intensity was observed upon ironing the fabric laundered with the encapsulated fragrance spheres of Example 1. Although odor intensity of the fabric laundered with the neat fragrance (control) was observed to be directly more intense, upon ironing, no significant increase in odor intensity was observed. Only a slight increase in odor intensity was observed when ironing the fabric laundered with the neat fragrance (control).

| Sample | One Week | Two Weeks |
| --- | --- | --- |
| Neat Fragrance (Control) | 2 | 1 |
| Encapsulated Fragrance (Example 1) | 6 | 5 |

At week one and week two the test results indicate that the cloth samples washed with the encapsulated fragrance of Example 1 are significantly more intense than the control samples washed with the neat fragrance (control). The products comprising the encapsulated fragrance show significant improvement over the performance of the neat fragrance in sustaining the volatile constituents of the fragrance and providing a prolong fragrance release from the dry laundered fabric over an extended period of time.

Incorporation of the Nano Spheres in Hair Care Products

EXAMPLE 6

The ability of the nano spheres of Example 2 to extend the release of the fragrance was determined by evaluating the menthol odor intensity retained on hair washed with a shampoo composition comprising the nano spheres of Example 2.

10 grams of the suspension of Example 2 is admixed with 90 grams of a shampoo base (30% concentrated shampoo base #4, product of JEEN International Corporation, of Little Fall, N.J. and 70% water) to create a shampoo sample containing 1.0% fragrance. A control sample was created by admixing 1.0 gram of fragrance with the above shampoo base.

Four hair swatches were washed with the shampoo sample comprising the nano-spheres of Example 2 and four hair swatches were washed with the control sample comprising the neat fragrance. Two of the hair swatches in each experimental set (two washed with the shampoo comprising the nano-spheres and two washed with the control sample) were dried using a blow dryer. The intensity of the fragrance retained on the wet swatches and the odor emitted 1 minute after drying the hair with a blow dryer was evaluated using a scale of 1 to 10, where 1 measures a low odor intensity and odor intensity of 10 measures a high intensity, pleasant odor. Odor perception is, by its nature, a very subjective determination and therefore needs to be determined by a panel of trained odor evaluator. According to the procedure, the hair swatches tested were provided to a panel of six odor evaluators who independently rank odor intensity retained on the wet hair swatches and in the proximate environment, 1 minute after blow drying the hair. The odor evaluation results were as follows:

|  | Wet Hair | One Minute After Blow-Drying |
|---|---|---|
| Neat Fragrance (Control) | 3 | 4 |
| Fragrance in Nano Spheres | 6 | 8 |

These results show that the hair swatches washed with the control samples, comprising the neat fragrance, had very low odor intensity. The hair swatches washed with the shampoo comprising the fragrance in the nano spheres had higher odor intensity. Thus, the nano spheres of the present invention adhere to hair and can be utilize to deposit higher level of fragrance onto hair. Only the hair swatches washed with the shampoo comprising the nano-spheres provided high impact fragrance "burst" upon blow drying the hair. Thus, the nano spheres of the present invention have the ability to provide heat triggered release of the active agents and yield high impact odor "burst" upon blow drying the hair or other type of heat treatment.

The other four hair swatches (washed with the shampoo comprising the nano-spheres and the control sample) were air-dried and odor intensity of the fragrance retained on the dry swatches was evaluated after one hour and after 8 hours using the same scale as above. According to the procedure, the hair swatches to be tested were provided to a panel of six odor evaluators who independently rank odor intensity retained on the hair swatches. The odor evaluation results after one hour and after 8 hours, on the dry hair swatches were as follows:

|  | Neat Fragrance (Control) | Fragrance in Nano Spheres |
|---|---|---|
| One Hour | 2 | 5 |
| 8 Hours | 1 | 4 |

These results show that the hair swatches washed with the control samples, comprising the neat fragrance, had very low odor intensity. The hair swatches washed with the shampoo comprising the fragrance in the nano spheres had higher odor intensity. Thus, the nano spheres of the present invention adhere to hair and can be utilize to deposit higher level of fragrance onto hair. Odor intensity of the hair swatches washed with the shampoo comprising the fragrance in the nano spheres, after 8 hours, was significantly higher than that of the swatches washed with these products comprising the neat fragrance. Also, Odor intensity of the hair swatches washed with the shampoo comprising the menthol in the nano spheres, remain almost the same as after one hour. Thus, the nano spheres of the present invention have the ability to sustain the release of active ingredients and provide extended release, even for volatile ingredients such as fragrances. The release rate of the fragrance, or other sensory markers, can be synchronize with that of the active agent to convey to the consumer the product performance.

EXAMPLE 8

The ability of the nano spheres of Example 2 to extend the release of active agents and sensory markers (i.e., a fragrance) was determined by evaluating the odor intensity retained on hair washed with a hair conditioner composition comprising the nano spheres of Example 2.

10 grams of the suspension of Example 2 is admixed with 90 grams of a conditioner base (40% Jeequat ASP, product of JEEN International Corporation, of Little Fall, N.J. and 60% water) to create a hair conditioner sample containing 1% fragrance. A control sample was created by admixing 1 gram of the neat fragrance with the above conditioner base.

Two hair swatches were washed with the conditioner sample comprising the nano spheres of Example 2 and two hair swatches were washed with the control sample comprising the neat fragrance. The hair swatches were air dried and odor intensity of the fragrance retained on the dry swatches was evaluated after one hour and after 24 hours. Odor perception is, by its nature, a very subjective determination. According to the procedure, the hair swatches to be tested were provided to a panel of six odor evaluators who independently rank odor intensity retained on the hair swatches using a scale of 1 (neutral, low odor intensity) to 10 (high, pleasant, odor intensity). The odor evaluation results after one hour and after 24 hours, on the dry hair swatches were as follows:

|  | Neat Fragrance (Control) | Fragrance in Nano Spheres |
|---|---|---|
| One Hour | 4 | 9 |
| 24 Hours | 3 | 8 |

These results show that the hair swatches washed with the control samples, comprising the neat fragrance, had very low odor intensity. The hair swatches washed with the conditioner comprising the fragrance in the nano spheres had higher odor intensity. Thus, the nano spheres of the present invention adhere to hair and can be utilize to deposit higher level of fragrance onto hair. Odor intensity of the hair swatches washed with the conditioner comprising the fragrance in the nano spheres, after 24 hours, was significantly higher than that of the swatches washed with these products comprising the neat fragrance. Also, Odor intensity of the hair swatches washed with the conditioner comprising the fragrance contained in the nano spheres, was almost as high as their odor intensity after one hour. Thus, the nano spheres of the present invention have the ability to sustain the release of active ingredients and provide extended release, even for volatile ingredients such as fragrances. The release rate of the fragrance, or other sensory markers, can be synchronize with that of ascorbic acid, or other active ingredients, to convey to the consumer the product performance.

It is understood that the above-described embodiments are illustrative of only a few of the many possible specific embodiments which can represent applications of the principles of the invention. Numerous and varied other arrangements can be readily derived in accordance with these principles by those skilled in the art without departing from the spirit and scope of the invention.

What is claimed is:

1. A controlled delivery system for use as a topical application to skin comprising:
   a solid sphere comprising a hydrophobic core containing an active agent and a cationic conditioning agent.

2. The system of claim 1 wherein said hydrophobic core comprises a hydrophobic polymer, hydrophobic copolymer, hydrophobic wax or a mixture thereof.

3. The system of claim 2 wherein said sphere has a melting point between about 30 degrees C. to about 100 degrees C.

4. The system of claim 2 wherein said hydrophobic polymer or hydrophobic copolymer is selected from a group consisting of: fatty acid esters, fatty alcohols, natural waxes, synthetic waxes, triglycerides, hydrogenated plant oils, biodegradable natural polymers, synthetic polymers, polyethylene homopolymers; ethylene-acrylic acid copolymer; polyamide polymer having a molecular weight in the range of from about 6,000 up to about 12,000; animal waxes, alkylated polyvinyl pyrrolid, silicon synthetic wax copolymer; silicon natural wax copolymer; candelilla silicon copolymer, and ozokerite silicon copolymer.

5. The system of claim 1 where said sphere has an average particle diameter of from about 0.01 micron to about 10 microns.

6. The system of claim 5 wherein said average particle diameter is from about 0.01 microns to about 1 micron.

7. The system of claim 1 wherein said system is a dispersion of a plurality of said solid spheres in an aqueous phase.

8. The system of claim 1 wherein said hydrophobic core further comprises a cationic charge booster.

9. The system of claim 8 wherein said cationic charge booster is selected from the group consisting of polyvinyl amine, polyamine, polyalkyleneamine, polyalkyleneimine, a poly-quaternary ammonium compound and a quaternary ammonium compound having the formula,

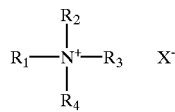

wherein X is an anion and $R_1$, $R_2$, $R_3$, and $R_4$ are each independently $C_1$–$C_{22}$ alkyl, $C_3$–$C_{22}$ alkenyl, or $R_5$—Q—$(CH_2)_m$—, wherein $R_5$ is $C_1$–$C_{22}$ alkyl or alkenyl moiety having from 1 to 22 carbon atoms, and mixtures thereof, m is from 1 to about 6;

and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

10. The system of claim 8 wherein said cationic charge booster comprises polyethyleneimine or polyethyleneamine.

11. The system of claim 1 comprising a cationic charge booster in an aqueous phase of a dispersion of said sphere.

12. The system of claim 11 wherein said cationic charge booster is selected from the group consisting of polyvinyl amine, polyamine, polyalkyleneamine, polyalkyleneimine, a poly-quaternary ammonium compound and a quaternary ammonium compound having the formula,

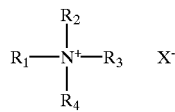

wherein X is an anion and $R_1$, $R_2$, $R_3$, and $R_4$ are each independently $C_1$–$C_{22}$ alkyl, $C_3$–$C_{22}$ alkenyl, or $R_5$—Q—$(CH_2)_m$—, wherein $R_5$ is $C_1$–$C_{22}$ alkyl or alkenyl moiety having from 1 to 22 carbon atoms, and mixtures thereof, m is from 1 to about 6;

and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

13. The system of claim 11 wherein said cationic charge booster comprises polyethyleneimine or polyethyleneamine.

14. The system of claim 11 wherein said cationic charge booster is present in an amount up to about 10% by weight of the aqueous phase.

15. The system of claim 1 wherein said cationic conditioning agent is selected from a group consisting of straight-chain alkylammonium compounds, cyclic alkylammonium compounds, petroleum derived cationic compounds, and cationic polymers.

16. The system of claim 1 wherein said cationic conditioning agent comprises cetyl trimethylammonium chloride.

17. The system of claim 1 wherein said cationic conditioning agent comprises behenamidopropyl hydroxyethyl dimonium chloride.

18. The system of claim 1 wherein said cationic conditioning agent comprises polyquaterium-24.

19. The system of claim 1 wherein said cationic conditioning agent comprises quaternium-82.

20. The system of claim 1 wherein the cationic conditioning agent is present in an amount of about 0.01% to about 70% by weight of the sphere.

21. The system of claim 1 wherein said active agent is selected from the group consisting of ceramides, sunscreens, drugs, vitamins, antioxidants, free radical scavengers, moisturizing agents, antiseborrhoeic agents, anti-UV agents, keratolytic agents, anti-inflammatory agents, refreshing agents, melanoregulators, liporegulators, antiseborrhoeic agents, anti-ageing agents, keratolytic agents, antibacterial agents, anti-dandruff agents, agents for combating hair loss, hair dyes, hair bleaches, reducing agents for permanent waves, hair conditioners, nutrients, cicatrizing agents, vascular protectors, antibacterial agents, anti fungal agents, skin conditioners, immunomodulators, nutrients, oils, retinoids, anesthetics, surfactants, emulsifiers, stabilizers, preservatives, antiseptics, emollients, lubricants, humectants, anesthetics, analgesics, enzymes, pigments, dyes, hydroxy acids, emollients, medications, antibiotics, repellants, attractants, fragrances, sensory markers, hyaluronic acid, hyaluronic acid salts, elastins, hydrolysates, primrose oil, jojoba oil, epidermal growth factor, soybean saponins, mucopolysaccharides, and mixtures thereof.

22. The system of claim 1 wherein said active agent comprises a fragrance.

23. The system of claim 22 wherein said fragrance has a ClogP in the range of about 1 to about 8.

24. The system of claim 2 wherein said hydrophobic polymer, hydrophobic copolymer or mixture thereof is present in an amount of about 1% to about 95% by weight, said cationic conditioning agent is present in an amount of about 0.01% to about 60% by weight, and said active agent is present in an amount of about 1% to about 70% by weight.

25. The system of claim 1 further comprising about 1% to about 70% by weight of a sensory marker in said hydrophobic core.

26. The system of claim 1 wherein said sphere releases said cationic conditioning agent over an extended period of time.

27. The system of claim 26 wherein said extended period of time is up to about 1 month.

28. The system of claim 1 wherein said sphere releases an effective amount of said cationic charge booster and said cationic conditioning agent to provide a burst upon heat treatment of said particle.

29. A method of producing a controlled release system for topical application to skin comprising the steps of:
heating a matrix material of a hydrophobic polymer to a temperature above the material melting point;
dissolving or dispersing a cationic conditioning agent into the melt;
dissolving or dispersing an active agent into the melt;
heating the melt to a temperature above the melting point of the melt;
mixing the hot melt with an aqueous solution to form a suspension;
high shear homogenization of the suspension at a temperature above the melting temperature until a homogeneous fine suspension is obtained; and
cooling the suspension to ambient temperature to create a fine dispersion.

30. The method of claim 29 wherein the aqueous solution further comprises a cationic charge booster.

31. A skin care product comprising the system of claim 1.

32. The product of claim 31 is selected from the group consisting of:
lotions, creams, and bodywash.

33. The product of claim 31 wherein said active agent comprises a sensory marker.

34. A controlled delivery system for fabric comprising:
a solid sphere comprising a hydrophobic core containing an active agent and a cationic conditioning agent.

35. The system of claim 34 wherein said hydrophobic core comprises a hydrophobic polymer, hydrophobic copolymer, hydrophobic wax or a mixture thereof.

36. The system of claim 35 wherein said sphere has a melting point between about 30 degrees C. to about 100 degrees C.

37. The system of claim 36 wherein said hydrophobic polymer or hydrophobic copolymer is selected from a group consisting of: fatty acid esters, fatty alcohols, natural waxes, synthetic waxes, triglycerides, hydrogenated plant oils, biodegradable natural polymers, synthetic polymers, polyethylene homopolymers; ethylene-acrylic acid copolymer; polyamide polymer having a molecular weight in the range of from about 6,000 up to about 12,000; animal waxes, alkylated polyvinyl pyrrolid, silicon synthetic wax copolymer; silicon natural wax copolymer; candelilla silicon copolymer, and ozokerite silicon copolymer.

38. The system of claim 34 where said sphere has an average particle diameter of from about 0.01 micron to about 10 microns.

39. The system of claim 38 wherein said average particle diameter is from about 0.01 microns to about 1 micron.

40. The system of claim 1 wherein said system is a dispersion of a plurality of said solid spheres in an aqueous phase.

41. The system of claim 1 wherein said solid sphere further comprises a cationic charge booster.

42. The system of claim 41 wherein said cationic charge booster is selected from the group consisting of polyvinyl amine, polyamine, polyalkyleneamine, polyalkyleneimine, a poly-quaternary ammonium compound and a quaternary ammonium compound having the formula,

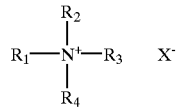

wherein X is an anion and $R_1$, $R_2$, $R_3$, and $R_4$ are each independently $C_1$–$C_{22}$ alkyl, $C_3$–$C_{22}$alkenyl, or $R_5$—Q—$(CH_2)_m$—, wherein $R_5$ is $C_1$–$C_{22}$ alkyl or alkenyl moiety having from 1 to 22 carbon atoms, and mixtures thereof, m is from 1 to about 6;
and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

43. The system of claim 34 wherein said cationic charge booster comprises polyethyleneimine or polyethyleneamine.

44. The system of claim 34 comprising a cationic charge booster in an aqueous phase of a dispersion of a plurality of said spheres.

45. The system of claim 44 wherein said cationic charge booster is selected from the group consisting of polyvinyl amine, polyamine, polyalkyleneamine, polyalkyleneimine, a poly-quaternary ammonium compound and a quaternary ammonium compound having the formula,

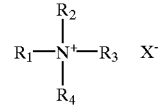

wherein X is an anion and $R_1$, $R_2$, $R_3$, and $R_4$ are each independently $C_1$–$C_{22}$ alkyl, $C_3$–$C_{22}$ alkenyl, or $R_5$—Q—$(CH_2)_m$—, wherein $R_5$ is $C_1$–$C_{22}$ alkyl or alkenyl moiety having from 1 to 22 carbon atoms, and mixtures thereof, m is from 1 to about 6;
and when taken together with the Q unit is an acyl unit, Q can be derived from a source of triglyceride selected from the group consisting of tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

46. The system of claim 45 wherein said cationic charge booster comprises polyethyleneimine or polyethyleneamine.

47. The system of claim 45 wherein said cationic charge booster is present in an amount up to about 10% by weight of the aqueous phase.

48. The system of claim 34 wherein said cationic conditioning agent is selected from a group consisting of straight-chain alkylammonium compounds, cyclic alkylammonium compounds, petroleum derived cationic compounds, and cationic polymers.

49. The system of claim 34 wherein said cationic conditioning agent comprises cetyl trimethylammonium chloride.

50. The system of claim 34 wherein said cationic conditioning agent comprises behenamidopropyl hydroxyethyl dimonium chloride.

51. The system of claim 34 wherein said cationic conditioning agent comprises polyquaterium-24.

52. The system of claim 34 wherein said cationic conditioning agent comprises quaternium-82.

53. The system of claim 34 wherein the cationic conditioning agent is present in an amount of about 0.01% to about 70% by weight of the sphere.

54. The system of claim 34 wherein said active agent comprises a fragrance.

55. The system of claim 54 wherein said fragrance has a ClogP in the range of about 1 to about 8.

56. The system of claim 35 wherein said hydrophobic polymer, hydrophobic copolymer or mixture thereof is present in an amount of about 1% to about 95% by weight, said cationic conditioning agents are present in an amount of about 0.01% to about 60% by weight, and said active agent is present in an amount of about 1% to about 70% by weight.

57. The system of claim 34 wherein said sphere releases said cationic conditioning agent over an extended period of time.

58. The system of claim 57 wherein said extended period of time is up to about 1 month.

59. The system of claim 34 wherein said sphere releases an effective amount of said cationic conditioning agent to provide a burst upon heat treatment of said particle.

60. A method of producing a controlled release system for fabric comprising the steps of:

heating a matrix material of a hydrophobic polymer to a temperature above the material melting point;

dissolving or dispersing a cationic conditioning agent into the melt; dissolving or dispersing an active agent into the melt;

heating the melt to a temperature above the melting point of the melt; mixing the hot melt with an aqueous solution to form a suspension;

high shear homogenization of the suspension at a temperature above the melting temperature until a homogeneous fine suspension is obtained; and cooling the suspension to ambient temperature to create a fine dispersion.

61. The method of claim 59 wherein the aqueous solution further comprises a cationic charge booster.

62. A fabric care product comprising the system of claim 34.

63. The product of claim 62 is selected from the group consisting of: liquid laundry detergents and fabric softeners.

* * * * *